(12) United States Patent
Falahee

(10) Patent No.: US 7,901,429 B2
(45) Date of Patent: Mar. 8, 2011

(54) WOUND AND SKIN CLOSURE INSTRUMENT AND METHOD OF USE

(75) Inventor: Mark H. Falahee, Ann Arbor, MI (US)

(73) Assignee: Medical Designs, LLC, Ann Arbor, MI (US)

( * ) Notice: Subject to any disclaimer, the term of this patent is extended or adjusted under 35 U.S.C. 154(b) by 1172 days.

(21) Appl. No.: 10/805,856

(22) Filed: Mar. 22, 2004

(65) Prior Publication Data
US 2004/0186406 A1 Sep. 23, 2004

Related U.S. Application Data

(60) Provisional application No. 60/456,611, filed on Mar. 22, 2003.

(51) Int. Cl.
*A61B 17/08* (2006.01)
*A61D 1/00* (2006.01)
(52) U.S. Cl. ........................................................ 606/213
(58) Field of Classification Search .......... 606/213–216, 606/134, 211, 201; 601/133, 118–119; 412/6, 412/37; 156/115; 128/888; 222/102, 201, 222/182; 118/218, 227, 262; 492/52; 523/105, 113, 118; D19/66–67, 70–71
See application file for complete search history.

(56) References Cited

U.S. PATENT DOCUMENTS

| | | | | |
|---|---|---|---|---|
| 2,303,131 A * | 11/1942 | Morgan | ........................ | 606/216 |
| 3,371,823 A * | 3/1968 | Petersen | ........................ | 222/97 |
| 3,591,878 A * | 7/1971 | Muhlbach et al. | ............... | 12/8.3 |
| 5,082,144 A * | 1/1992 | Sundstrom | ...................... | 222/99 |
| 6,558,398 B1 * | 5/2003 | Espinoza | ...................... | 606/133 |

* cited by examiner

*Primary Examiner* — Todd E Manahan
*Assistant Examiner* — L. Bachman
(74) *Attorney, Agent, or Firm* — Gifford, Krass, Sprinkle, Anderson & Citkowski, P.C.

(57) ABSTRACT

A skin closure instrument and method of use are disclosed. Broadly a tool grasps skin edges and applies glue evenly in rapid and reproducible fashion, thereby enabling a single healthcare provider to perform the procedure. In the preferred embodiment, the instrument is packaged in a sterile container for a single use. The glue may be packaged along with the instrument, or may be added to a reservoir. The system is applicable to both small and large wounds, and is easy to manipulate by a single operator, resulting in a rapid consistent closure of wound edges.

3 Claims, 1 Drawing Sheet

WOUND AND SKIN CLOSURE INSTRUMENT AND METHOD OF USE

REFERENCE TO RELATED APPLICATION

This application claims priority from U.S. Provisional Patent Application Ser. No. 60/456,611, filed Mar. 22, 2003, the entire content of which is incorporated herein by reference.

FIELD OF THE INVENTION

This invention relates generally to wound closure and in particular, to a skin closure instrument, preferably disposable, and method of use.

BACKGROUND OF THE INVENTION

According to current practice, two basic techniques are used to close wounds, whether resulting from trauma or surgical procedures. Either sutures or staples are applied to the edges of the skin, or a adhesive such as Dermabond (super glue) is used. Both of these approaches present problems, however. Sutures and staples require removal, and considerable time is required for application. Particularly in light of the need for removal, a larger scar potential arises.

Skin glue, on the other hand, requires holding the skin edges together while, at the same time, applying the glue. Repeated pinching and glue application is time-consuming, and can lead to inconsistent closure areas. Accordingly, this approach is not practical for larger wounds. Moreover, the use of glue often requires additional subcutaneous sutures to help hold wound edges well apposed, adding to the labor-intensive nature of the technique.

The need remains, therefore, for an improved wound and skin closure apparatus and method.

SUMMARY OF THE INVENTION

This invention improves upon the prior art by providing a disposable skin closure instrument and method of use. Broadly the tool grasps skin edges and applies glue evenly in rapid and reproducible fashion, thereby enabling a single healthcare provider to perform the procedure. In the preferred embodiment, the instrument is packaged in a sterile container for a single use. The glue may be packaged along with the instrument, or may be added to a reservoir. The system is applicable to both small and large wounds, and is easy to manipulate by a single operator, resulting in a rapid consistent closure of wound edges.

DETAILED DESCRIPTION OF THE INVENTION

In the preferred embodiment, the invention utilizes a pair of opposing, manually operated skin-pinching devices, over which there is disposed a supply of glue. Starting at the one of the wound, the skin-pinching devices are squeezed to close the wound, while the glue is applied from above. The apparatus is then moved along the length of the wound, with the glue continuing to be supplied, thereby closing the edges of the skin on contact.

Figures 1, 2:
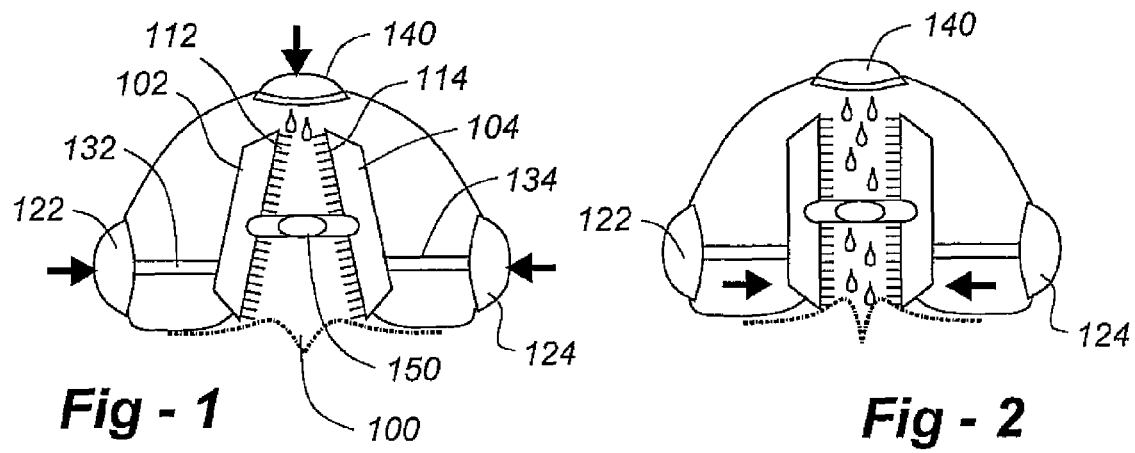
FIG. 1 depicts a skin-pinching device according to the invention including rotating wheels with staple hooks or projections.
FIG. 2 shows how a wound is closed.
Figure 3:
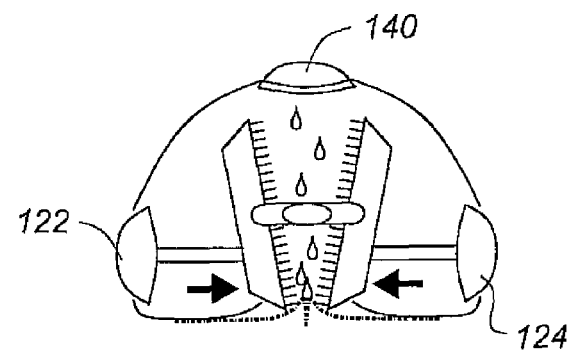
FIG. 3 best illustrates how side buttons allows the wheels to hook the skin, thereby more effectively squeezing the edges together as the glue is applied.
Figure 4:
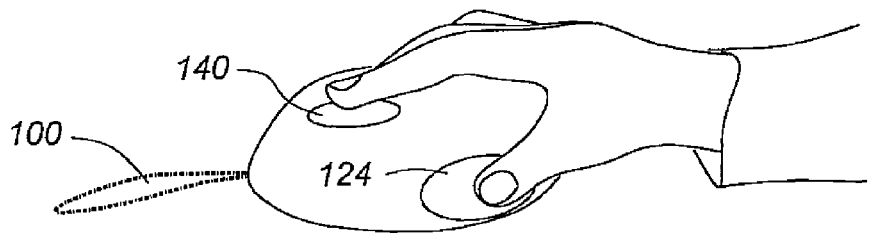
FIG. 4 shows the device in use.

Making reference to FIG. 1, the skin-pinching devices take the form of rotating wheels 102, 104 each of which preferably include staple hooks or projections 112, 114. The wheels are preferably spring-biased at the angles shown in FIG. 1, with the axle 150 being of the type having ball/socket connections to the wheels to permit such rotation. The wheels are preferably coupled to side buttons 122, 124, enabling the wheels to be compressed while rotating, thereby closing the wound 100. The use of the side buttons allows the wheels to reverse their angles as shown in FIG. 3 to hook the skin, thereby more effectively squeezing the edges together as the glue is applied.

The glue may be released in different ways, either by crushing a vial of glue or, with the use of a reservoir which may be filled as necessary so as to flow down onto the skin edges as they come together. The various components are preferably contained in some sort of a clear and/or flexible housing including a midline indicator, enabling the tool to be pulled slowly along the wound while keeping the instrument on alignment. Pulling the tool along rotates the wheels, thereby continually bringing fresh edges of apposing skin together, with the fast-acting glue closing and sealing the edges on contact.

In terms of the method, deep fascia or subcutaneous layers of the wound are closed in the usual fashion, as necessary. The skin at one end of the wound is then grasped and slightly elevated to help engage the tool described above, which is then applied to the wound. A top button 140 is pressed to break the vial of glue to be released, or, alternatively, to release glue from a reservoir.

The side buttons are compressed to bring the rotating wheels into capture of the skin edges, and the instrument is then pulled in line directly over the wound, preferably at a slow and steady motion to the opposite end, with the directional indicators or midline markings of the tool serving as a guide. When the end of the wound is reached, the side buttons are released, at which time the tool may be turned around and reapplied in the opposite direction as necessary. In the preferred embodiment, the tool is disposable, and, following the procedure, bandages may be applied as necessary.

I claim:

1. An instrument for closing skin edges forming a wound, the instrument comprising:
   a pair of opposing, wheels that rotate in the same direction, enabling the instrument to be pulled along a wound to progressively bring skin edges together;
   a breakable vial or fillable reservoir of skin glue; and
   a device to supply the glue to the skin edges being brought together.

2. The instrument of claim 1, wherein the wheels include barbs or other skin-engaging features.

3. The instrument of claim 1, wherein the wheels are coupled to opposing manually operated buttons.

* * * * *